United States Patent [19]
Roth et al.

[11] Patent Number: 4,735,958
[45] Date of Patent: Apr. 5, 1988

[54] TRANS-6-[2-[2-(SUBSTITUTED-PHENYL)-3- (OR 4-) HETEROARYL-5-SUBSTITUTED-1H-PYRROL-1-YL]-ETHYL]TETRAHYDRO-4-HYDROXY-2H-PYRAN-2-ONE INHIBITORS OF CHOLESTEROL BIOSYNTHESIS

[75] Inventors: Bruce D. Roth, Ann Arbor; Drago R. Sliskovic, Ypsilanti, both of Mich.

[73] Assignee: Warner-Lambert Company, Morris Plains, N.J.

[21] Appl. No.: 944,318

[22] Filed: Dec. 22, 1986

[51] Int. Cl.$^4$ .................. A61K 31/395; A61K 31/44; C07D 405/14
[52] U.S. Cl. .................................. 514/343; 514/256; 514/314; 514/414; 514/422; 544/333; 546/167; 546/281; 548/466; 548/527
[58] Field of Search .................. 546/281; 514/343

[56] References Cited

U.S. PATENT DOCUMENTS 4,613,610  9/1986  Wareing .............................. 514/406
4,647,576  3/1987  Hoefle et al. ....................... 514/343

FOREIGN PATENT DOCUMENTS 8402131  11/1983  PCT Int'l Appl. .
8600307   1/1986. PCT Int'l Appl. .

Primary Examiner—Glennon H. Hollrah
Assistant Examiner—James H. Turnipseed
Attorney, Agent, or Firm—Jerry F. Janssen

[57] ABSTRACT

Certain trans-6-[2-[2-(substituted-phenyl)-3- (or 4-)heteroaryl-5-substituted-1H-pyrrol-1-yl]ethyl]tetrahydro-4-hydroxy-2H-pyran-2-ones and the corresponding lactone-ring-opened acids are potent inhibitors of the enzyme 3-hydroxy-3-methylglutaryl-coenzyme A reductase (HMG CoA reductase) and are thus useful hypolipidemic or hypocholesterolemic agents. Pharmaceutical compositions containing such compounds, and a method of inhibiting the biosynthesis of cholesterol employing such pharmaceutical compositions are also disclosed.

9 Claims, No Drawings

TRANS-6-[2-[2-(SUBSTITUTED-PHENYL)-3- (OR 4-) HETEROARYL-5-SUBSTITUTED-1H-PYRROL-1-YL]-ETHYL]TETRAHYDRO-4-HYDROXY-2H-PYRAN-2-ONE INHIBITORS OF CHOLESTEROL BIOSYNTHESIS

BACKGROUND OF THE INVENTION

The present invention is related to compounds and pharmaceutical compositions useful as hypocholesterolemic and hypolipidemic agents. More particularly, this invention concerns certain trans-6-[2-[2-(substituted-phenyl)-3- (or 4-)heteroaryl-5-substituted-1H-pyrrol-1-yl]ethyl]tetrahydro-4-hydroxy-2H-pyran-2-ones and the corresponding lactone-ring-opened acids which are potent inhibitors of the enzyme 3-hydroxy-3-methylglutaryl-coenzyme A reductase (HMG CoA reductase), pharmaceutical compositions containing such compounds, and a method of inhibiting the biosynthesis of cholesterol employing such pharmaceutical compositions.

High levels of blood cholesterol and blood lipids are conditions involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine*, 305, No. 9, 515–517 (1981). It has now been established that lowering LDL-C levels affords protection from coronary heart disease (cf. *Journal of the American Medical Association*, 251, No. 3, 351–374 (1984).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer et al., *Proc. Soc. Exper. Biol. Med.*, 102: 270 (1959) and F. H. Hulcher, Arch. Biochem. Biophys., 146: 422 (1971)).

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown et al., *J. Chem. Soc. Perkin I* (1976) 1165.

U.S. Pat. No. 4,255,444 to Oka et al. discloses several synthetic derivatives of mevalonolactone having antilipidemic activity.

U.S. Pat. No. 4,198,425 and 4,262,013 to Mitsue et al. disclose aralkyl derivatives of mevalonolactone which are useful in the treatment of hyperlipidemia.

U.S. Pat. No. 4,375,475 to Willard et al. discloses certain substituted 4-hydroxytetrahydropyran-2-ones which, in the 4(R)-trans-stereoisomeric form, are inhibitors of cholesterol biosynthesis.

Published PCT application WO 86/00307 discloses certain pyrazole analogs and derivatives of mevalonolactone having utility as hypolipoproteinemic and antiatherosclerotic agents.

SUMMARY OF THE INVENTION

In accordance with the present invention, there are provided certain trans-6-[2-[2-(substituted-phenyl)-3- (or 4-)heteroaryl-5-substituted-1H-pyrrol-1-yl]ethyl]tetrahydro-4-hydroxy-2H-pyran-2-ones and the corresponding lactone-ring-opened hydroxy-acids which are potent inhibitors of cholesterol biosynthesis by virtue of their ability to inhibit the enzyme 3-hydroxy-3-methylglutaryl coenzyme A reductase (HMG-CoA reductase).

In particular, in its broadest aspect the present invention provides compounds of structural formula I

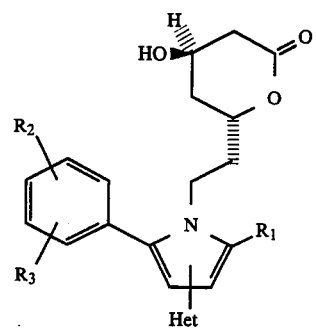

wherein $R_1$ is alkyl of from one to four carbon atoms, cyclopropyl, or trifluoromethyl.

$R_2$ and $R_3$ are independently selected from hydrogen, alkyl of from one to four carbon atoms, chlorine, and fluorine.

Het is a heteroaromatic ring selected from

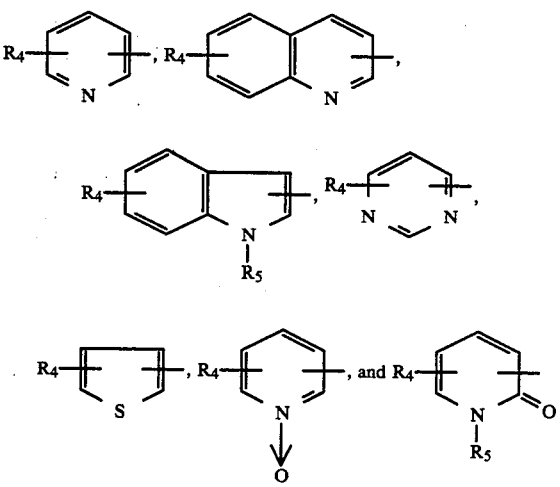

where $R_4$ and $R_5$ are hydrogen or alkyl of from one to four carbon atoms.

Also contemplated as falling within the scope of the present invention are the hydroxy acids, and pharmaceutically acceptable salts thereof, corresponding to the opening of the lactone ring of the compounds of structural formula I above.

In yet another aspect, the present invention provides pharmaceutical compositions useful as hypolipidemic or hypocholesterolemic agents comprising a hypolipidemic or hypocholesterolemic effective amount of a compound in accordance with this invention as set forth above, in combination with a pharmaceutically acceptable carrier.

In another aspect, the present invention provides a method of inhibiting cholesterol biosynthesis in a patient in need of such treatment by administering an effective amount of a pharmaceutical composition as defined above.

DETAILED DESCRIPTION

The compounds of the present invention comprise a class of trans-6-[2-[2-(substituted-phenyl)-3- (or 4-)heteroaryl-5-substituted-1H-pyrrol-1-yl]ethyl]tetrahydro-4-hydroxy-2H-pyran-2-ones and the corresponding lactone-ring-opened hydroxy-acids in which the heterocyclically-substituted pyrrole nucleus is attached, through an ethylene group to the remainder of the molecule. Preferred compounds of the present invention are those in which the heterocyclic substituent is 2-, 3-, or 4-pyridyl.

In the compounds of the present invention, $R_1$ is substituted with alkyl of from one to four carbon atoms, cyclopropyl, or trifluoromethyl. The preferred substituent at this position is 1-methylethyl.

$R_2$ and $R_3$ in compounds of the present invention are independently selected from alkyl of from one to four carbon atoms, fluorine, or chlorine. Preferred compounds of the present invention are those in which $R_2$ is fluorine and $R_3$ is hydrogen.

The compounds of structural formula I above possess two asymmetric carbon centers, one at the 4-hydroxy position of the pyran-2-one ring, and the other at the 6-position of the pyran-2-one ring where the alkylpyrrole group is attached. This asymmetry gives rise to four possible isomers, two of which are the R-cis- and S-cis-isomers and the other two of which are the R-trans- and S-trans-isomers. This invention contemplates only the trans-form of the compounds of formula I above.

Examples of compounds contemplated as falling within the scope of the present invention include, but are not limited to the following:

trans-(±)-6-[2-[2-(4-Fluorophenyl)-5-(1-methylethyl)-3-(2-pyridinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-3-(3-pyridinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-3-(4-pyridinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-4-(2-pyridinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-4-(3-pyridinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-4-(4-pyridinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-3-(3-quinolinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-3-(4-quinolinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-3-(2-thienyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-3-(3-thienyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-3-(5-pyrimidinyl)-1H-pyrrol-1-yl]ethyl]tetrahydro-4-hydroxy-2H-pyran-2-one.

trans-(±)-6-[2-[2-(4-Fluorophenyl)-5-(1-methylethyl)-4-(5-pyrimidinyl)-1H-pyrrol-1-yl]ethyl]tetrahydro-4-hydroxy-2H-pyran-2-one.

The reaction sequence which is used to prepare compounds of the present invention is depicted schematically in the following reaction sequences. The general method outlined in Reaction Sequence 1 is used to prepare compounds of the present invention in which The substituted phenyl ring and the heterocyclic substituent are attached to adjacent positions on the pyrrole nucleus. Alternatively, the general method employed for preparing compounds of the present invention where the heterocyclic substituent and $R_1$ are attached to adjacent positions of the pyrrole nucleus is shown in Reaction Sequence 2.

Referring to Reaction Sequence 1, the β-ketoester, 2, is condensed with the desired heterocyclic carboxaldehyde, represented in the reaction sequence by pyridine-2-carboxaldehyde, 3, to produce the condensation product, 4. This reaction is generally carried out in diethyl ether at temperature of between about 0° C. and 5° C. for period of from 5–10 hours in the presence of a base such as piperidine.

The condensation product, 4, is further condensed with the desired substituted benzaldehyde, 5, to produce 6. The reaction is generally run in the absence of a solvent at temperatures ranging from 50° C. to about 100° C., preferably about 70° C. and for a period of about 24 hours. The details of this reaction are dicussed more fully in H. Stetter, *Ang. Chem.*, 15 (11): 639–712 (1976).

The diketoester, 6, is dissolved in a 5:1 mixture of tetrahydrofuran/methanol and then treated with aqueous sodium hydroxide at room temperature for about 24 hours to hydrolyze the ester and to effect decarboxylation to produce 7.

Compound 7 is reacted with the diethyl acetal of 3-aminopropanal to produce the substituted pyrrole compound, 8. This reaction is carried out for about 24 hours in boiling toluene with concurrent azeotropic removal of the water which is formed in the reaction.

The acetal, 8, is hydrolyzed to the corresponding pyrrole-aldehyde, 9, by the action of 2:1 tetrahydrofuran/1M hydrochloric acid. The pyrrole-aldehyde, 9, is reacted with the dilithium or lithio-sodio salt of methyl acetoacetate, 10, to produce the corresponding 7-(substituted-pyrrolyl)-5-hydroxy-3-oxoleptanoates, 11.

Reaction Sequence 1
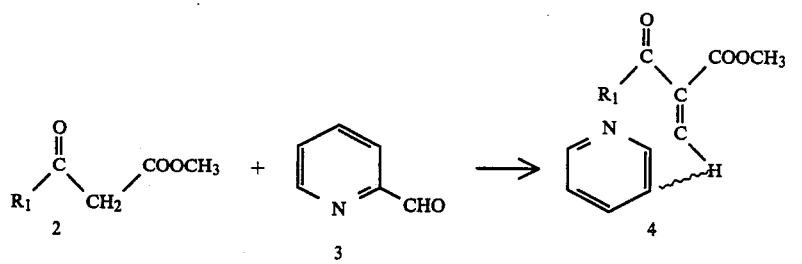
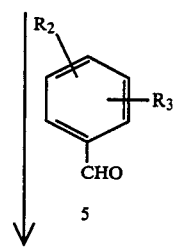
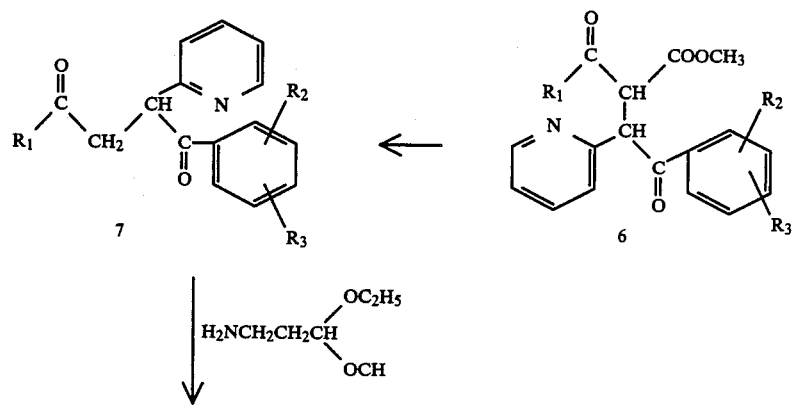
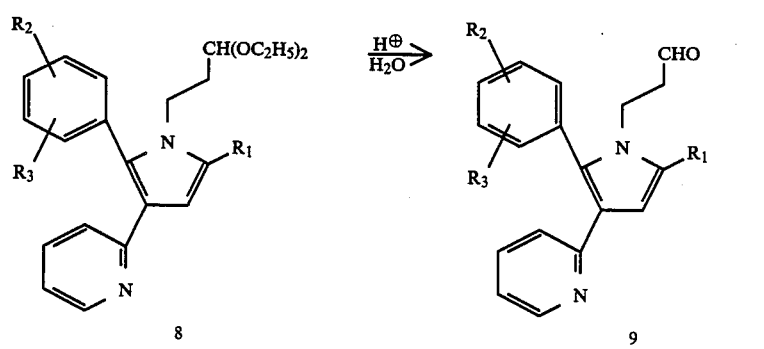
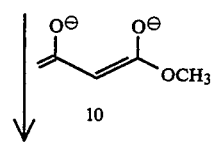

-continued
Reaction Sequence 1

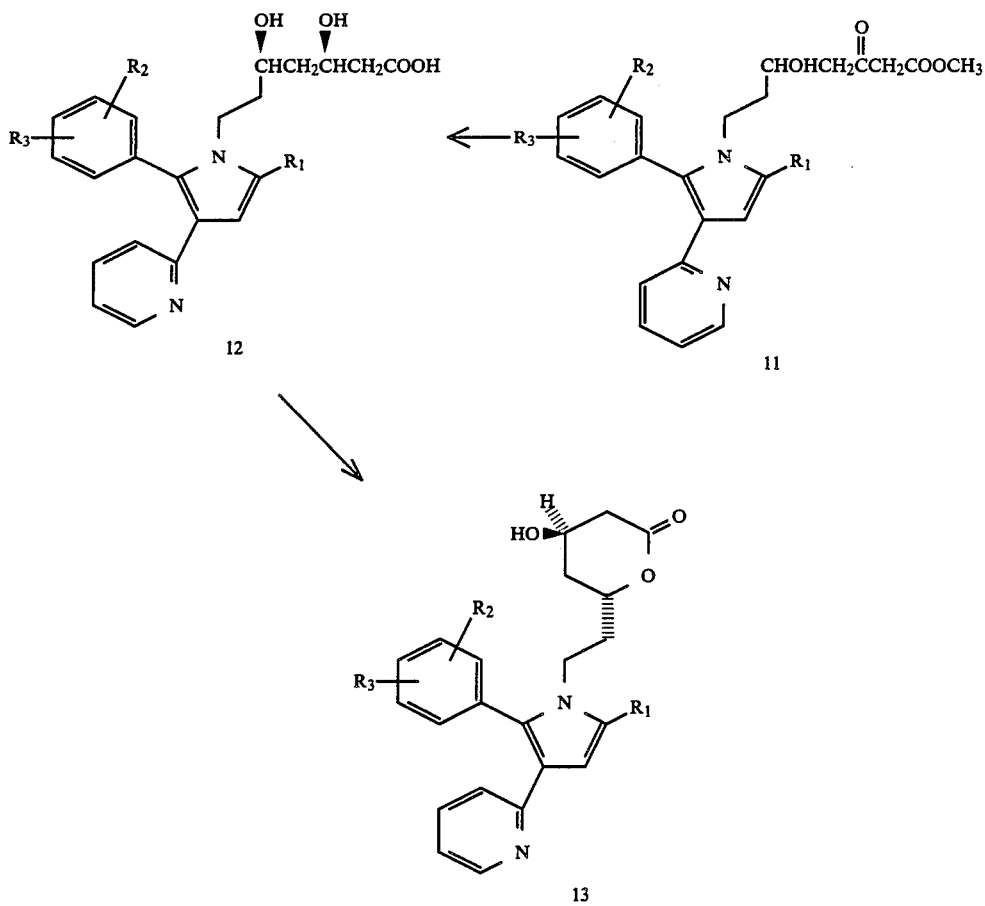

The heptanoate, 11, is dissolved in a polar solvent such as tetrahydrofuran, through which a small amount of air has been bubbled. A slight excess of a trialkylborane, such as triethyl- or tributylborane, is added to the mixture which is then cooled to a temperature of preferably between about 0° C. and −78° C. after which sodium borohydride is added.

The mixture is stirred for about one to two hours and then oxidized by the addition of basic aqueous hydrogen peroxide solution. The reaction produces the B 7-(substituted-pyrrolyl)-3,5-dihydroxyheptanoic acids, 12, in which the product contains a predominance of the desired R*,R* configuration at carbon atoms three and five bearing the hydroxy groups.

The acids, 12, may be converted to a corresponding pharmaceutically acceptable salt by conventional means, if desired, and used as pharmaceutical agents according to the present invention, or cyclized to the trans-6-[2-[2-(substituted-phenyl)-3- or (4-)heteroaryl-5-substituted-1H-pyrrol-1-yl]ethyl]tetrahydro-4-hydroxy-2H-pyran-2-ones, 13 by dehydration in an inert solvent such as refluxing toluene with azeotropic removal of water. This cyclization step has been found to produce material containing from 85–90% of the desired trans-configuration of the 4-hydroxy group relative to the 6-(substituted-pyrrol-1-yl)alkyl group on the pyran-2-one lactone ring.

Referring now to Reaction Sequence 2, an analogous series of reactions are carried out to produce compounds of the present invention where the heterocyclic substituent and the substituent, $R_1$, are attached to adjacent atoms of the pyrrole nucleus. However, in this reaction sequence, the starting materials are the substituted $\beta$-ketoesters, 14, and the heterocyclically-substituted aldehydes, 15.

The starting materials for reactions shown in Reaction Sequences 1 and 2 are known or, if not previously known, are made by reactions well known to practitioners of the chemical art.

Reaction Sequence 2
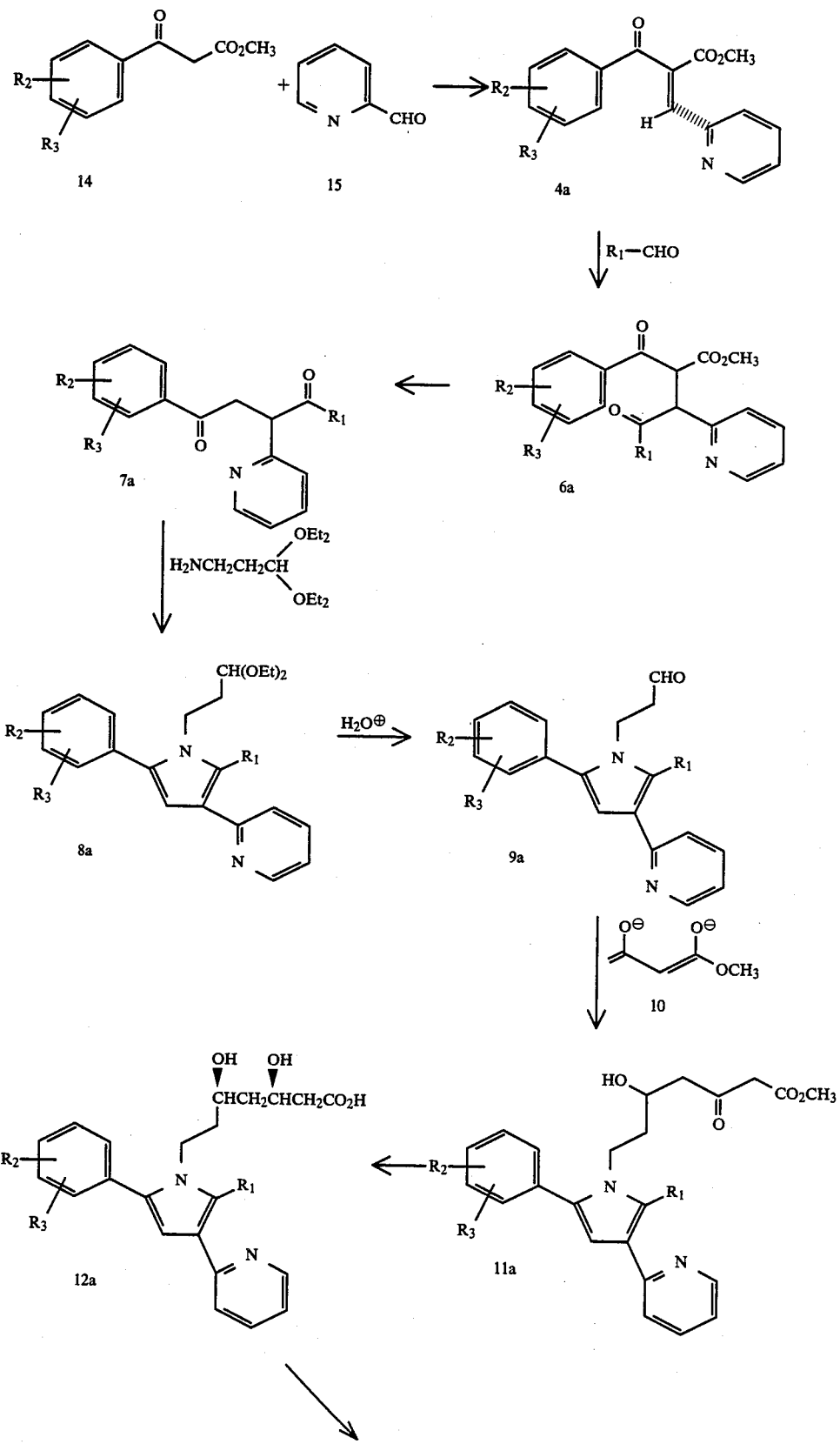

-continued
Reaction Sequence 2

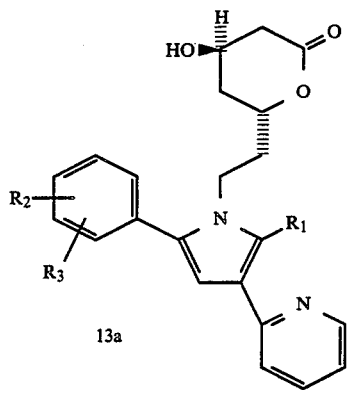

13a

The compounds of the present invention where the heterocyclic group is a pyridine-N-oxide or an alkylsubstituted pyridine-N-oxide are prepared from the corresponding pyridine compounds by conventional means such as oxidation of the latter with m-chloroperbenzoic acid.

The compounds of this invention where the heterocyclic group is an N-alkyl-substituted pyridinone are prepared by conventional means from the corresponding pyridine compounds by N-alkylation with an alkyl halide followed by oxidation of the resulting N-alkylpyridinium salt with potassium ferricyanide.

The ring-opened hydroxy acids of structural formulae 12 and 12a above are intermediates in the synthesis of the lactone compounds of formulae 13 and 13a and may be used in their free acid form or in the form of a pharmaceutically acceptable metal or amine salt in the pharmaceutical method of the present invention. These acids react to form pharmaceutically acceptable metal and amine salts. The term "pharmaceutically acceptable metal salt" contemplates salts formed with the sodium, potassium, calcium, magnesium, aluminum, iron, and zinc ions. The term "pharmaceutically acceptable amine salt" contemplates salts with ammonia and organic nitrogenous bases strong enough to form salts with carboxylic acids. Bases useful for the formation of pharmaceutically acceptable nontoxic base addition salts of compounds of the present invention form a class whose limits are readily understood by those skilled in the art. See, for example, S. M. Berge et al., *J. Pharm. Sci.*, 66: 1-19 (1977).

The free acid form of compounds of the present invention may be regenerated from the salt form, if desired, by contacting the salt with a dilute aqueous solution of an acid such as hydrochloric acid.

The base addition salts may differ from the free acid forms of the compounds of this invention in such properties as melting point or solubility in polar solvents such as water, but are otherwise considered equivalent for the purposes of this invention.

The compounds of the present invention may exist in solvated or unsolvated form. In general, the solvated forms with pharmaceutically acceptable solvents such as water, ethanol and the like, are equivalent to the unsolvated forms for the purposes of this invention.

The compounds of this invention are useful as hypocholesterolemic or hypolipidemic agents by virtue of their ability to inhibit the biosynthesis of cholesterol through inhibition of the enzyme 3-hydroxy-3-methylglutaryl-coenzyme A reductase (HMG-CoA reductase).

The ability of compounds of the present invention to inhibit the biosynthesis of cholesterol was measured by the procedure described by R. E. Dugan et al., *Archiv. Biochem. Biophys.*, (1972), 152, 21-27. In this method, designated CSI, the level of HMG-CoA enzyme activity in standard laboratory rats is increased by feeding the rats a chow diet containing 5% cholestyramine for four days, after which the rats are sacrificed.

The rat livers are homogenized, and the incorporation of cholesterol-$^{14}$C-acetate into nonsaponifiable lipid by the rat liver homogenate is measured. The micromolar concentration of compound required for 50% inhibition of sterol synthesis over a one-hour period is measured, and expressed as an IC$_{50}$ value.

The activity of representative examples of compounds in accordance with the present invention appears in Table 1, and is compared with that of the prior art compound, compactin.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

TABLE 1

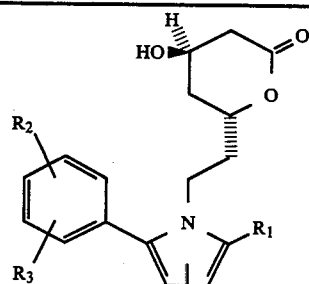

| Compound | $R_1$ | $R_2$ | $R_3$ | HET | CSI $IC_{50}$ |
|---|---|---|---|---|---|
| 1 | 1-Methylethyl | H | 4-Fluorophenyl | 3-(2-Pyridinyl) | $4.8 \times 10^{-8}$ M |
| 2 | 1-Methylethyl | H | 4-Fluorophenyl | 3-(3-Pyridinyl) | $5.5 \times 10^{-8}$ M |
| 3 | 1-Methylethyl | H | 4-Fluorophenyl | 3-(4-Pyridinyl) | $1.3 \times 10^{-8}$ M |
| Compactin (Prior art) | | | | | $1.8 \times 10^{-8}$ M |

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid form preparations include solutions suitable for oral or parenteral administration, or suspensions and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as hypolipidemic or hypocholesterolemic agents, the compounds utilized in the pharmaceutical method of this invention are administered to the patient at dosage levels of from 40 mg to 600 mg per day. For a normal human adult of approximately 70 kg or body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of trans-(±)-6-[2-[2-(4-Fluorophenyl)-5-(1-methylethyl)-3-(2-pyridinyl)-1H-pyrrol-1-yl]ethyl]tetrahydro-4-hydroxy-2H-pyran-2-one Step A—Preparation of 2-(2-methyl-1-oxopropyl)-3-(2-pyridinyl)propenoic acid, methyl ester Piperidine (1 ml) was added to a stirred solution of 4-methyl-2-oxo-pentanoic acid, methyl ether (43 g, 298 mmol) and 28.6 ml (300 mmol) of pyridine-2-carboxaldehyde in 60 ml of diethyl ether maintained at 0° C.

The resulting mixture was maintained at 0° C. for three days and then concentrated under vacuum to yield 66 g of crude product. This material was dissolved in toluene and filtered through silica gel to remove the colored impurities. The solvent was removed under vacuum to yield 46 g of 2-(2-methyl-1-oxopropyl)-3-(2-pyridinyl)propenoic acid, methyl ester.

The 90 MHz proton magnetic resonance spectrum of the product (CDCl$_3$ solution) indicated the predominance of a single diastereomer and exhibited peaks at 1.20 (doublet, 6 protons), 2.85 (septet, 1 proton), 3.78 (singlet, 3 protons), 6.9–7.4 (multiplet, 2 protons), 7.55 (singlet, 1 proton), 7.62 (multiplet, 1 proton), and 8.45 (multiplet, 1 proton) parts per million downfield from the tertramethyl-silane signal.

The infrared spectrum of a thin film of the product exhibited principal absorption peaks at 1726 and 1695 reciprocal centimeters.

Step B—Preparation of 1-(4-fluorophenyl)-5-methyl-2-(2-pyridinyl)hexane-1,4-dione To a solution of 15.4 g (66 mmol) of 2-(2-methyl-1-oxopropyl)-3-(2-pyridinyl)propenoic acid, methyl ester, 6.5 ml (46.2 mmol) of triethylamine and 8.2 g (66 mmol) of 4-fluorobenzaldehyde was added 15 mole percent of 3-benzyl-5-(2-hydroxyethyl)-4-methyl-1,3-thiazolium chloride (Aldrich Chemical Co., Milwaukee, WI, USA). The resulting mixture was heated at 70° C. for 3 hours, cooled, dissolved in ethyl acetate and washed successively with brine and water. The organic layer was separated, dried to yield the crude products an oil. The material was redissolved in 300 ml of tetrahydrofuran, and 150 ml of water and 6.6 g (165 mmol) of sodium hydroxide were added. This mixture was vigorously stirred overnight, concentrated, and the residue dissolved in a mixture of diethyl ether and ethyl acetate. The extract was washed with water and then extracted with 2M hydrochloric acid. The acid extract was made alkaline and extracted with diethyl ether. The ether extract was evaporated to yield 7.2 g (36%) of 1-(4-fluorophenyl)-5-methyl-2-(2-pyridinyl)hexane-1,4-dione.

The 90 MHz proton magnetic resonance spectrum of the product (CDCl$_3$ solution) exhibited peaks at 1.07 (doublet, 3 protons), 1.10 (doublet, 3 protons), 2.60 (septet, 1 proton), 2.85 (doublet of doublets, 2 protons), 3.58 (doublet of doublets, 2 protons), 5.20 (doublet of doublets, 1 proton), 6.8–7.2 (multiplet, 4 protons), 7.47 (multiplet, 1 proton), 7.95 (multiplet, 2 protons), and 8.40 (multiplet, 1 proton) parts per million downfield from the tetramethyl-silane signal.

The infrared spectrum of a thin film of the produce exhibited principal absorption peaks at 2960, 1710, 1680, 1595, 1230, and 1150 reciprocal centimeters.

Step C—Preparation of 3-[2-(4-fluorophenyl)-5-(1-methylethyl)-3-(2-pyridinyl)-1H-pyrrol-1-yl]-1-propanal, dimethyl acetal A mixture of 7.2 g (24 mmol) of the diketone from Step B, 4.3 g (36 mmol) of 3-aminopropanol dimethyl acetal, and 0.1 g of p-toluenesulfonic acid in 30 ml of toluene was stirred and heated under reflux with azeotropic removal of water for 6 hours. After this time the mixture was cooled, filtered through silica gel, eluting with a large volume of toluene, and evaporated to yield 7.3 g (79.6%) of 3-[2-(4-fluorophenyl)-5-(1-methylethyl)-3-(2-pyridinyl)-1H-pyrrol-1-yl]-1-propanal, dimethyl acetal.

The 90 MHz proton magnetic resonance spectrum of the product (CDCl$_3$ solution) exhibited peaks at 1.26 (doublet, 6 protons), 1.4–1.7 (multiplet, 2 protons), 2.95 (septet, 1 proton), 3.10 (singlet, 6 protons), 3.74 (multiplet, 2 protons), 6.51 (singlet, 1 proton), 6.5–7.3 (multiplet, 7 protons), and 8.40 (multiplet, 1 proton) parts per million downfield from the tetramethylsilane signal.

Step D—Preparation of 3-[2-(4-fluorophenyl)-5-(1-methylethyl)-3-(2-pyridinyl)-1H-pyrrol-1-yl]-1-propanal The dimethyl acetal (7.3 g, 19 mmol) from Step C was dissolved in 90 ml of 2:1 tetrahydrofuran/1M HCl and the resulting mixture was stirred at room temperature for 48 hours. The solution was then concentrated to remove the tetrahydrofuran, diluted with water, and extracted with diethyl ether. The aqueous layer was cooled and then adjusted to pH 8 with solid sodium bicarbonate. The resulting aqueous solution was extracted twice with ethyl acetate and the extracts were washed with brine and then dried. Concentration of the ethyl acetate solution yielded 5.95 g (93%) of 3-[2-(4-fluorophenyl)-5-(1-methylethyl)-3-(2-pyridinyl)-1H-pyrrol-1-yl]-1-propanal. This material solidified upon standing and, after recrystallization from isopropyl ether, had a melting point of 120°–122° C.

The 90 MHz proton magnetic resonance spectrum of the product (CDCl$_3$ solution) exhibited peaks at 1.30 (doublet, 6 protons), 2.48 (triplet, 2 protons), 2.82 (septet, 1 proton), 4.05 (multiplet, 2 protons), 6.51 (singlet, 1 proton), 6.5–7.3 (multiplet, 7 protons), 8.42 (multiplet, 1 proton), and 9.44 (singlet, 1 proton) parts per million downfield from the tetramethylsilane signal.

The infrared spectrum of the product exhibited principal absorption peaks at 1710, 1591, 1501, 1216, and 783 reciprocal centimeters.

Step E—Preparation of 7-[2-(4-fluorophenyl)-5-(1-methylethyl)-3-(2-pyridinyl)-1H-pyrrol-1-yl]-5-hydroxy-3-oxoheptanoic acid, ethyl ester A solution of 3.41 ml (26.55 mmol) of ethyl acetoacetate in 10 ml of dry tetrahydrofuran was added dropwise to a stirred suspension of sodium hydride (0.67 g, 28 mmol) in 20 ml of tetrahydrofuran at 0° C. under nitrogen. When gas evolution had ceased, 11.6 ml of a 2.3M solution of n-butyl lithium in hexane was added dropwise. The deep orange solution was stirred for 1 hour, cooled to −78° C., and 5.95 g (17.7 mmol) of the pyrrole aldehyde from Step D in 30 ml of dry tetrahydrofuran was added dropwise over a period of 15 minutes.

The resulting solution was stirred for 30 minutes and then allowed to warm to 0° C. The reaction was quenched by the addition of 1 ml of acetic acid followed by 30 ml of 2M hydrochloric acid. The resulting mixture was partitioned between 200 ml of diethyl ether and 100 ml of water. The ether layer was separated, extracted with 1M hydrochloric acid and the aqueous solutions combined and adjusted to pH 7–8 by the addition of solid sodium bicarbonate.

This aqueous solution was extracted with ethyl acetate, washed with brine and dried to yield 7.8 g (94%) of 7-[2-(4-fluorophenyl)-5-(1-methylethyl)-3-(2-pyridinyl)-1H-pyrrol-1-yl]-5-hydroxy-3-oxoheptanoic acid, ethyl ester.

The 90 MHz proton magnetic resonance spectrum of the product (CDCl₃ solution) exhibited peaks at 1.1–1.3 (multiplet, 9 protons), 1.3–1.6 (multiplet, 2 protons), 2.40 (doublet, 2 protons), 2.85 (septet, 1 protons), 3.27 (singlet, 2 protons), 3.7–3.9 (multiplet, 3 protons), and 4.10 (quartet, 2 protons) parts per million downfield from the tetramethylsilane signal.

Step F—Preparation of trans-(±)-6-[2-[2-(4-fluorophenyl)-5-(1-methylethyl)-3-(2-pyridinyl)-1H-pyrrol-1-yl]ethyl]-tetrahydro-4-hydroxy-2H-pyran-2-one Air (5 ml) was bubbled through a solution of the β-ketoester (7.8 g, 16.7 mmol) from Step E and 18.4 ml of a 1M tetrahydrofuran solution of tributylborane in 20 ml of tetrahydrofuran at room temperature under nitrogen.

The resulting mixture was stirred for 18 hours at room temperature, and then cooled to −78° C. To the cooled solution was added 0.7 g (20.2 mmol) of sodium borohydride in one portion. The mixture was vigorously stirred and allowed to warm slowly to 0° C. Acetic acid (3.6 ml) was added, followed by 3M sodium hydroxide solution and 6.1 ml of 30% hydrogen peroxide solution. The resulting mixture was allowed to stand at room temperature overnight, after which time it was partitioned between diethyl ether and water. The aqueous layer was acidified and extracted with diethyl ether. The aqueous layer was carefully neutralized with sodium bicarbonate and extracted several times with ethyl acetate. The extracts were combined, dried, and evaporated. The residual oil was heated 6 hours under reflux in toluene with azeotropic removal of the water which was formed. The solution was then concentrated to 5 ml and 0.5 ml of diisopropyl ether was added. Upon standing, 0.75 g of trans-(±)-6-[2-[2-(4-fluorophenyl)-5-(1-methylethyl)-3-(2-pyridinyl)-1H-pyrrol-1-yl]ethyl]tetrahydro-4-hydroxy-2H-pyran-2-one separated as colorless crystals, mp 186°–187° C.

Analysis: Calc. for $C_{25}H_{27}FN_2O_3$: C, 71.07%; H, 6.44%; N, 6.63%; Found: C, 70.67%; H, 6.69%; N, 6.40%.

EXAMPLE 2

Preparation of trans-(±)-6-[2-[2-[(4-Fluorophenyl)-5-(1-methylethyl)-3-(3-pyridinyl)-1H-pyrrol-1-yl]ethyl]tetrahydro-4-hydroxy-2H-pyran-2-one Employing the methods of Example 1, but starting with pyridine-3-carboxaldehyde in Step A, the title compound was prepared, mp 70°–74° C.

Analysis: Calc. for $C_{25}H_{27}FN_2O_3$: C, 71.07%; H, 6.44%; N, 6.63%; Found: C, 71.53%; H, 6.54%; N, 6.10%.

EXAMPLE 3

Preparation of trans-(±)-6-[2-[2-(4-Fluorophenyl)-5-(1-methylethyl)-3-(4-pyridinyl)-1H-pyrrol-1-yl]ethyl]tetrahydro-4-hydroxy-2H-pyran-2-one Employing the methods of Example 1, but starting with pyridine-4-carboxaldehyde in Step A, the title compound was prepared, mp 174°–176° C.

Analysis: Calc. for $C_{25}H_{27}FN_2O_3$: C, 71.07%; H, 6.44%; N, 6.63%; Found: C, 70.11%; H, 6.54%; N, 6.23%.

We claim:

1. A compound of structural formula I

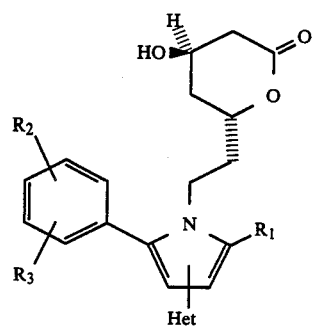

wherein $R_1$ is alkyl of from one to four carbon atoms, cyclopropyl, or trifluoromethyl;

$R_2$ and $R_3$ are independently selected from hydrogen, alkyl of from one to four carbon atoms, chlorine, and fluorine;

Het is a heteroaromatic ring selected from

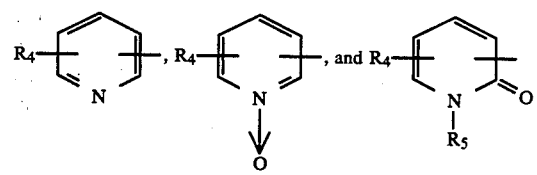

where $R_4$ and $R_5$ are hydrogen or alkyl of from one to four carbon atoms; or the corresponding lactone-ring opened hydroxy acid and the pharmaceutically acceptable salts thereof.

2. A compound as defined by claim 1 wherein Het is

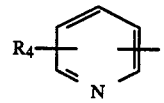

wherein $R_4$ is hydrogen or alkyl of from one to four carbon atoms.

3. A compound as defined by claim 1 wherein Het is

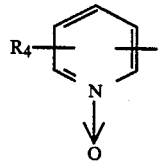

wherein $R_4$ is hydrogen or alkyl of from one to four carbon atoms.

4. A compound as defined by claim 1 wherein Het is

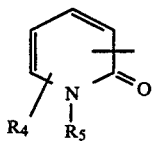

wherein R₄ and R₅ are independently selected from hydrogen and alkyl of from one to four carbon atoms.

5. A compound as defined by claim 2 having the name trans-(±)-6-[2-[2-(4-fluorophenyl)-5-(1-methylethyl)-3-(2-pyridinyl)-1H-pyrrol-1-yl]ethyl]tetrahydro-4-hydroxy-2H-pyran-2-one.

6. A compound as defined by claim 2 having the name trans-(±)-6-[2-[2-(4-fluorophenyl)-5-(1-methylethyl)-3-(3-pyridinyl)-1H-pyrrol-1-yl]ethyl]tetrahydro-4-hydroxy-2H-pyran-2-one.

7. A compound as defined by claim 2 having the name trans-(±)-6-[2-[2-(4-fluorophenyl)-5-(1-methylethyl)-3-(4-pyridinyl)-1H-pyrrol-1-yl]ethyl]tetrahydro-4-hydroxy-2H-pyran-2-one.

8. A pharmaceutical composition, useful as a hypocholesterolemic agent, comprising a hypocholesterolemic effective amount of a compound in accordance with claim 1 in combination with a pharmaceutically acceptable carrier.

9. A method of inhibiting cholesterol biosynthesis in a patient in need of such treatment by administering a pharmaceutical composition as defined by claim 8.

* * * * *